(12) United States Patent
Buettler et al.

(10) Patent No.: US 8,764,752 B2
(45) Date of Patent: Jul. 1, 2014

(54) PROTECTION SLEEVE HOLDING MECHANISM

(75) Inventors: Markus Buettler, Solothurn (CH); Simone Volzer, Solothurn (CH); Andreas Baeriswyl, Bettlach (CH)

(73) Assignee: Depuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/188,104

(22) Filed: Jul. 21, 2011

(65) Prior Publication Data
US 2012/0022533 A1 Jan. 26, 2012

Related U.S. Application Data

(60) Provisional application No. 61/366,997, filed on Jul. 23, 2010.

(51) Int. Cl.
*A61B 17/56* (2006.01)
(52) U.S. Cl.
USPC .............................. 606/62; 606/96
(58) Field of Classification Search
USPC ........................ 606/62–68, 96–98
See application file for complete search history.

(56) References Cited

U.S. PATENT DOCUMENTS

| | | | |
|---|---|---|---|
| 4,672,957 A | 6/1987 | Hourahane | |
| 4,911,153 A | 3/1990 | Border | |
| 4,920,958 A | 5/1990 | Walt et al. | |
| 4,945,904 A | 8/1990 | Bolton et al. | |
| 5,112,337 A | 5/1992 | Paulos et al. | |
| 5,154,720 A | 10/1992 | Trott et al. | |
| 5,163,940 A | 11/1992 | Bourque | |
| 5,234,434 A | 8/1993 | Goble et al. | |
| 5,350,380 A | 9/1994 | Goble et al. | |
| 5,458,602 A | 10/1995 | Goble et al. | |
| 5,613,971 A | 3/1997 | Lower et al. | |
| 6,039,739 A | 3/2000 | Simon | |
| 6,210,417 B1 | 4/2001 | Baudino et al. | |
| 6,254,605 B1 * | 7/2001 | Howell | 606/96 |
| 6,379,360 B1 | 4/2002 | Ackeret et al. | |
| 7,232,443 B2 | 6/2007 | Zander et al. | |
| 7,549,994 B2 | 6/2009 | Zander et al. | |
| 2003/0069581 A1 * | 4/2003 | Stinson et al. | 606/62 |
| 2003/0073999 A1 * | 4/2003 | Putnam | 606/62 |

(Continued)

FOREIGN PATENT DOCUMENTS

| | | |
|---|---|---|
| WO | 2011/046784 | 4/2001 |
| WO | 2004/045384 | 6/2004 |

*Primary Examiner* — Jerry Cumberledge
*Assistant Examiner* — Nicholas Plionis
(74) *Attorney, Agent, or Firm* — Fay Kaplun & Marcin, LLP

(57) ABSTRACT

A system for inserting an intramedullary nail into a bone includes (a) a handle extending from a proximal end to a distal end configured to couple to an intramedullary nail only in a desired orientation and (b) an aiming device extending from a proximal end to a distal end configured for attachment to the proximal end of the handle. The aiming device includes a guide opening extending therethrough sized and shaped to accommodate a protective sleeve therein. The guide opening is located and oriented so that, when the aiming device and the handle are coupled to one another, a bone fixation receiving hole in an intramedullary nail coupled to the handle is aligned with the guide opening. The aiming device further includes a locking pin fixedly mounted thereto. The locking pin extends into the guide opening to engage a protective sleeve inserted therein.

15 Claims, 3 Drawing Sheets

(56) References Cited

U.S. PATENT DOCUMENTS

| | | |
|---|---|---|
| 2004/0059329 A1 | 3/2004 | Zander |
| 2004/0204711 A1* | 10/2004 | Jackson .................... 606/61 |
| 2005/0096656 A1* | 5/2005 | Behrens .................... 606/64 |
| 2005/0119663 A1 | 6/2005 | Keyer et al. |
| 2005/0261698 A1 | 11/2005 | Powell |
| 2008/0015588 A1* | 1/2008 | Hawkes .................... 606/64 |
| 2008/0154264 A1 | 6/2008 | Wack et al. |
| 2008/0300629 A1* | 12/2008 | Surti ...................... 606/232 |
| 2011/0245878 A1* | 10/2011 | Franks et al. ............ 606/278 |

* cited by examiner

US 8,764,752 B2

PROTECTION SLEEVE HOLDING MECHANISM

PRIORITY CLAIM

The present application claims priority to U.S. Provisional Application Ser. No. 61/366,997 filed on Jul. 23, 2010 and entitled "Protection Sleeve Holding Mechanism," the entire disclosure of which is incorporated herein by reference.

FIELD OF THE INVENTION

The present invention relates to the treatment of bone fractures and, in particular, relates to a device for guiding a bone drill and/or other instruments used during a bone fixation process.

BACKGROUND

Intramedullary nails are often employed to stabilize long bones (e.g., femur or tibia) after a fracture. Intramedullary nails generally include a transverse hole through which a locking bone fixation element is inserted into the surrounding bone to fix the intramedullary nail within the bone. The bone may be pre-drilled to receive the locking bone fixation element using an aiming arm as a guide with a protective sleeve inserted into an opening of the aiming arm to prevent damage to surrounding tissue while the bone is being pre-drilled.

However, these protective sleeves sometimes fall out of the aiming arm and may drop to the ground making the protective sleeve unsterile and unfit for further use. This requires that the protective sleeve be held in place by a surgeon, nurse or other technician during pre-drilling increasing the difficulty of the procedure.

SUMMARY OF THE INVENTION

The present invention relates to a system for inserting an intramedullary nail into a bone, comprising a handle extending from a proximal end to a distal end configured to couple to an intramedullary nail only in a desired orientation and an aiming device extending from a proximal end to a distal end configured for attachment to the proximal end of the handle, the aiming device including a guide opening extending therethrough sized and shaped to accommodate a protective sleeve therein, the guide opening being located and oriented so that, when the aiming device and the handle are coupled to one another, a bone fixation receiving hole in an intramedullary nail coupled to the handle is aligned with the guide opening, the aiming device further including a locking pin fixedly mounted thereto, the locking pin extending into the guide opening to engage a protective sleeve inserted therein.

DETAILED DESCRIPTION

Figure 1:
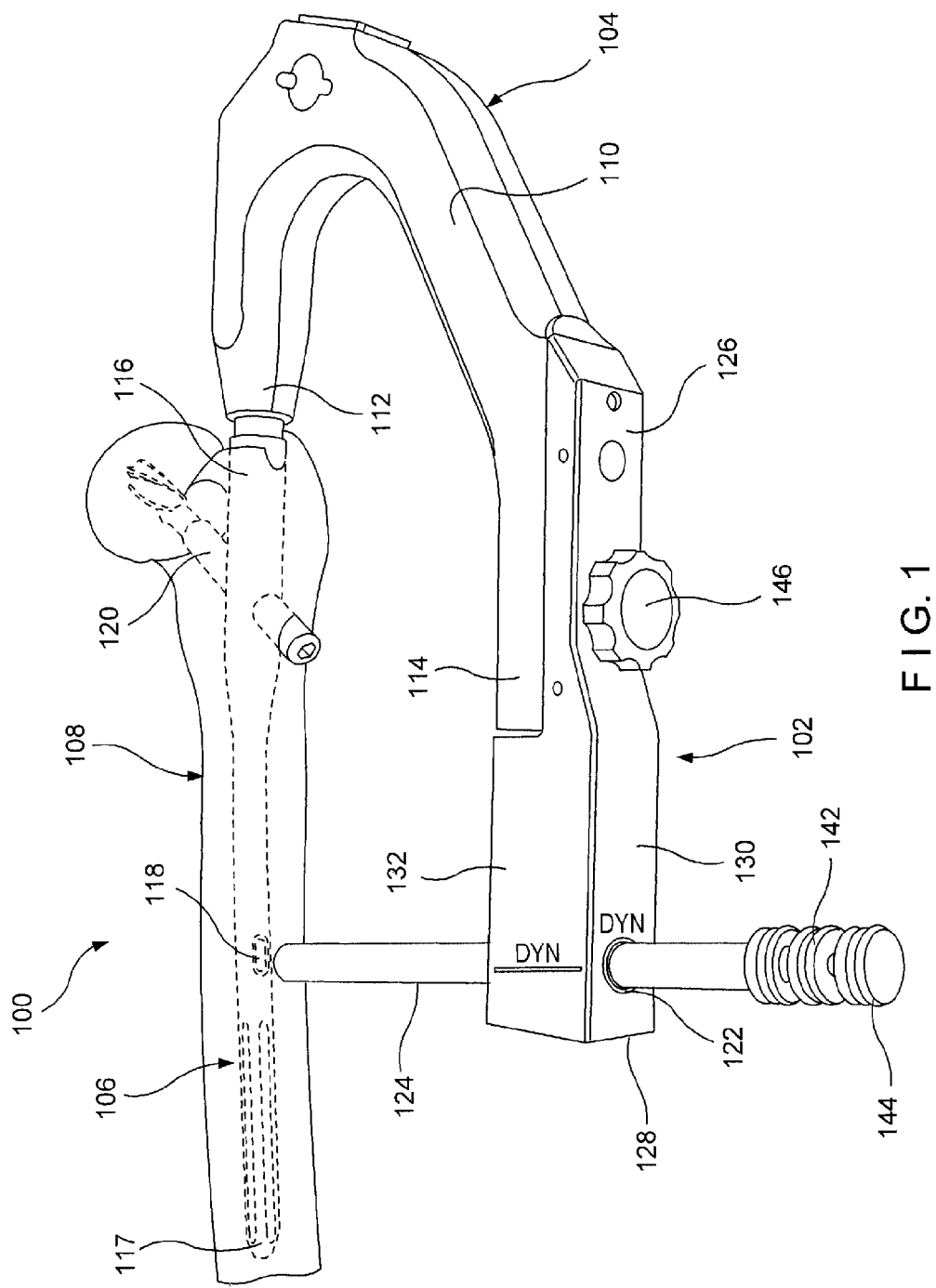
FIG. 1 shows a perspective view of a system according to an exemplary embodiment of the present invention.

The present invention may be further understood with reference to the following description and the appended drawings, wherein like elements are referred to with the same reference numerals. The present invention relates to the treatment of bone fractures and, in particular, relates to a device for guiding a bone drill and/or other instruments used during a bone fixation process. Exemplary embodiments of the present invention describe an aiming device including a guide opening that receives and holds a sleeve therein. It will be understood by those of skill in the art that although the exemplary embodiments described herein specifically describe an aiming device for an intramedullary nail, the aiming device of the present invention may also be used with a plate system or other bone fixation device. It should also be noted that the terms "proximal" and "distal" as used herein, refer to a direction towards (proximal) and away from (distal) a surgeon or other user.

As shown in FIGS. 1-6, a system 100 according to an exemplary embodiment of the invention comprises an aiming device 102 and a handle 104 configured to be employed in inserting into a long bone an intramedullary nail 106. As shown in FIG. 1, the aiming device 102 is attachable to the handle 104, which is coupled to a proximal end 116 of the intramedullary nail 106 to facilitate insertion thereof into the medullary canal of a bone 108. The aiming device 102 and the handle 104 are attachable to one another only in a desired orientation relative to one another and the handle 104 couples to the intramedullary nail 106 in a specific orientation so that a guide opening 122 of the aiming device 102 is substantially aligned with a hole 118 extending transversely through the intramedullary nail 106. That is, the aiming device 102 and the handle 104 are sized and shaped with respect to an intramedullary nail to be used therewith so that, when coupled to one another, the guide opening 122 is positioned to serve as a drilling guide. Specifically, a drilling instrument may be inserted through the guide opening 122 to pre-drill a hole in the bone 108 in alignment with the hole 118 of the nail 106. Thus, a bone fixation element may be inserted through this pre-drilled hole in the bone 108 into the hole 118 of the intramedullary nail 106 to fix the intramedullary nail 106 in a desired position within the bone 108. The system 100 further comprises a sleeve such as, for example, protective sleeve 124 insertable through the opening 122 as well as a drill sleeve 142 and a trocar 144, each of which may be co-axially received within the protective sleeve 124. It will be understood by those of skill in the art that, although the drill sleeve 142 and trocar 144 may be removed during the surgical process, the protective sleeve 124 is maintained within the guide opening 122 to protect surrounding tissues during the drilling and/or bone fixation element insertion. To prevent the protective sleeve 124 from inadvertently falling out of the guide opening 122 during the surgical process, the aiming arm 102 includes a pin 140 disposed therewithin, which engages the sleeve 124 to hold the protective sleeve 124 in position within the guide opening 122.

The handle 104 includes a substantially curved body 110, which extends from a first end 112 adapted and configured to be coupled to a proximal end 116 of the intramedullary nail 106 to a second end 114 adapted and configured to be coupled to the aiming device 102. The handle 104 permits a surgeon or other user of the system 100 to insert the intramedullary nail 106 to a desired position within the medullary canal of the bone 108. The curved body 110 of the handle 104 allows the surgeon to exert both a longitudinal and rotational force on the intramedullary nail 106 until the nail 106 is in the desired position and rotational orientation within the medullary canal.

The intramedullary nail 106 extends longitudinally from a proximal end 116 which is coupleable to the handle 104 to a distal end 117 and, as described above, includes at least one hole 118 extending transversely therethrough sized and shaped to accommodate a bone fixation element such as, for example, a screw, nail or pin. It will be understood by those of skill in the art that the intramedullary nail 106 may include any number of holes 118 along a length thereof and that the aiming device 102 may include various guide openings 122 positioned to align with any or all of these various holes 118 or to align with the holes 118 of differently sized intramedullary nails. It will also be understood by those skilled in the art that the aiming device 102 and the handle 104 may be configured to work with a variety of types and sizes of intramedullary nails 106 which may be used to stabilize bone (e.g., for a variety of different types of fractures). For example, the intramedullary nail 106 may be used to fix a fracture along a length of the bone 108 or may be used in conjunction with another implant 120 (e.g., hip implant) to fix a fracture through a head portion of the bone 108.

Figure 2:
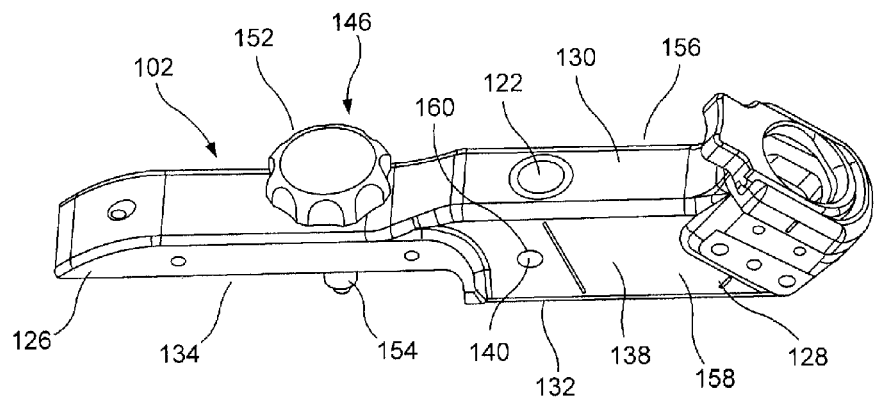
FIG. 2 shows a perspective view of an aiming device of the system of FIG. 1.
Figure 3:
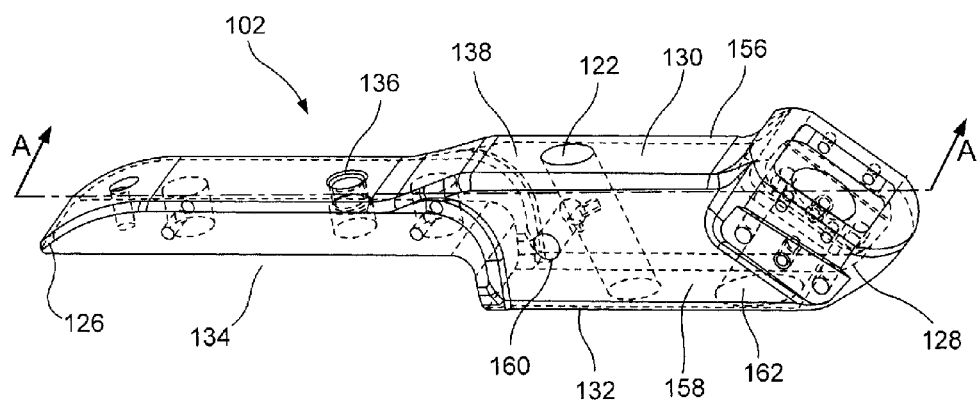
FIG. 3 shows a transparent perspective view of the aiming device of FIG. 2.
Figure 4:
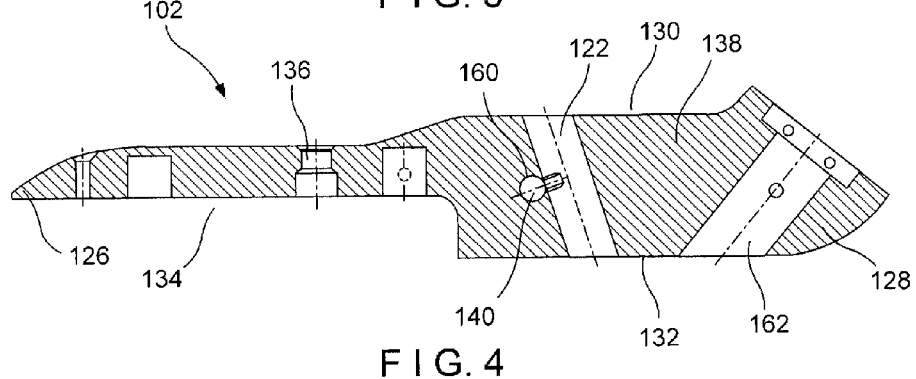
FIG. 4 shows a cross sectional view of the aiming device of FIG. 2, along line A-A.

As shown in FIGS. 2-4, the aiming device 102 extends longitudinally from a first end 126 to a second end 128 with the first end 126 being attachable to the handle 104 via a coupling element 146. The aiming device 102 includes a first surface 130 which, when in an operative configuration, faces away from the bone 108 and a second surface 132 which, when in the operative configuration, faces the bone 108. The aiming device 102 further includes a third surface 156 and a fourth surface 158, each of which extend laterally relative to the first and second surfaces 126, 128 to connect the first and second surfaces 126, 128 on opposing sides. The guide opening 122 extends through the aiming device 102 from the first surface 130 to the second surface 132. It will be understood by those of skill in the art that the aiming device 102 may include other openings 162 extending therethrough for aiming and guiding other devices and/or instruments such as, for example, the implant 120. The aiming device 102 further includes a pin opening 160 extending through the aiming device 102 between the third surface 156 and the fourth surface 158. In a preferred embodiment, the pin opening 160 may not extend entirely through the aiming device 102. For example, the pin opening 160 may be a blind hole that extends from one of the third and fourth surfaces 156, 158 but does not break through to the other.

The aiming device 102 may include a recess 134 extending from the first end 126 along a portion of a length the second surface 132 sized and shaped to engage a corresponding portion of the handle 104. The aiming device 102 further includes an opening 136 extending therethrough, from the first surface 130 to the second surface 132 of the recess 134. The opening 136 may be sized and shaped to receive a portion of the coupling element 146 therethrough to couple the aiming device 102 to the handle 104.

The coupling element 146 according to this embodiment includes a knob 152 with a shaft portion 154 extending therefrom. The shaft portion 154 is insertable through the opening 136 of the aiming device 102 to couple the aiming device 102 to the handle 104. The shaft portion 154 includes, for example, threading along a portion thereof for engaging a correspondingly threaded opening within the handle 104. Thus, a user may rotate the knob 152 to selectively couple and de-couple the aiming device 102 from the handle 104, as would be understood by those of skill in the art. It will also be understood by those of skill in the art, however, that the coupling element 146 may take any of a variety of forms so long as the coupling element 146 facilitates attachment of the aiming device 102 to the handle 104. In another embodiment, the aiming device 102 and the handle 104 may be integrally formed such that a coupling element 146 is not required.

The guide opening 122 extends through a non-recessed portion 138 of the aiming device 102, from the first surface 130 to the second surface 132. The guide opening 122 is sized and shaped to receive the protective sleeve 124 therein. In a preferred embodiment, the protective sleeve 124 is substantially tubular and the guide opening 122 is substantially cylindrical with an inner diameter slightly greater than an outer diameter of the protective sleeve 124. It will be understood by those of skill in the art, however, that the protective sleeve 124 and the guide opening 122 may take any of a variety of shapes so long as the protective sleeve is slidably receivable within the guide opening 122. As described above, the aiming device 102 may include a plurality of guide openings 122 to correspond to the locations of more than one hole 118 in the intramedullary nail 106.

Figure 5:
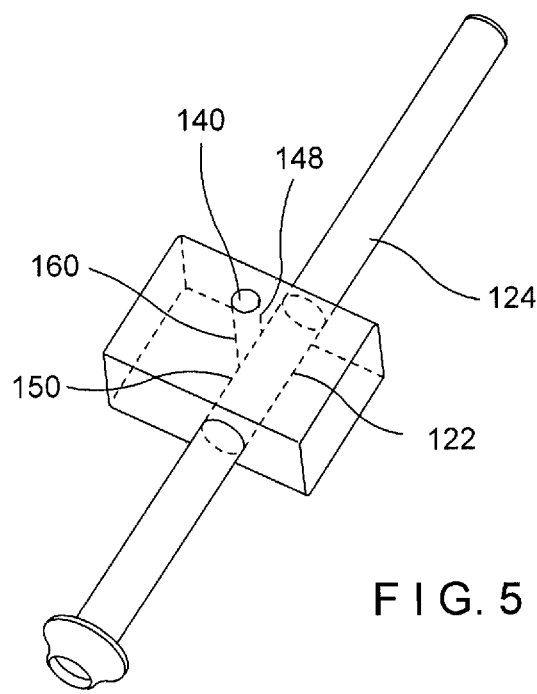
FIG. 5 shows a perspective view of a pin of the aiming device of FIG. 2 engaging a sleeve inserted through the aiming device.
Figure 6:
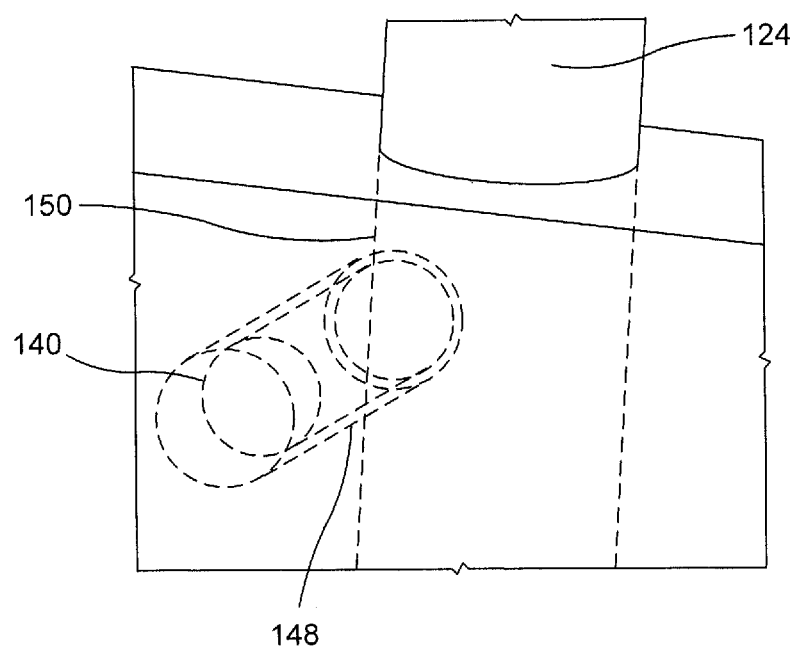
FIG. 6 shows an enlarged perspective view of the pin and sleeve of FIG. 5.

The pin opening 160 which extends through the aiming device 102 between the third and fourth lateral surfaces 156, 158 is sized and shaped to accommodate the pin 140. The pin opening 160 extends through a portion of the aiming device 102 transverse to the guide opening 122 such that a portion of the pin opening 160 overlaps with a portion of the guide opening 122, as shown in FIGS. 5-6. A length of the pin opening 160 and the pin 140 is selected such that the pin 140 passes an axis of the guide opening 122. Thus, the pin 140 is insertable into the pin opening 160 such that a portion of an outer surface 148 of the pin 140 extends transversely into the guide opening 122.

The pin 140 may be substantially tubular, including a lumen extending therethrough, and formed of a material including elastic properties such that the pin 140 may be compressed against the protective sleeve 124, exerting a force on the protective sleeve 124 and holding the protective sleeve 124 within the guide opening 122 when the protective sleeve 124 is inserted therethrough. The pin 140 may be held in position within the aiming device 102 by any suitable means (e.g., adhesive, friction fit) so that the pin 140 does not move relative thereto. Thus, when the protective sleeve 124 is inserted into the guide opening 122, an outer surface 150 of the protective sleeve presses against and compresses the outer surface 148 of the pin 140 such that the protective sleeve 124 is held in place within the guide opening 122. A force exerted by the pin 140 on the protective sleeve 124 may be adjusted by varying a wall thickness of the pin 140.

It will be understood by those of skill in the art that fixing the pin relative to the aiming device 102 as described above will prevent contamination and facilitate easy cleaning of the aiming device 102. It will also be understood by those of skill in the art that fixing the pin 140 relative to the aiming device 102 eliminates moving parts such that disassembly would not be required.

The pin 140 is fixed within the pin opening 160 so that a portion of the outer surface 148 thereof extends radially into the guide opening 122. A protective sleeve 124 is inserted into the guide opening 122 such that the outer surface 150 of the protective sleeve 124 presses against and compresses the pin 140 as the protective sleeve 124 is inserted therethrough. The pin 140 permits the protective sleeve 124 to be manually inserted and removed through the guide opening 122 while also exerting enough force on the protective sleeve 124 such that the pin 140 holds the protective sleeve 124 in position once the protective sleeve 124 has been slid into a desired position within the guide opening 122 preventing the sleeve 124 from being inadvertently dropped from the aiming device 102.

It will be understood by those skilled in the art that various modifications and variations can be made in the structure and the methodology of the present invention, without departing from the spirit or scope of the invention. Thus, it is intended that the present invention cover the modifications and variations of this invention provided that they come within the scope of the appended claims and their equivalents.

What is claimed is:

1. A system for inserting an intramedullary nail into a bone, comprising:
    a handle extending from a proximal end to a distal end configured to couple to an intramedullary nail only in a desired orientation; and
    an aiming device extending from a proximal end to a distal end configured for attachment to the proximal end of the handle, the aiming device including a guide opening extending therethrough along a guide opening axis, the guide opening being sized and shaped to accommodate a protective sleeve therein, the guide opening being located and oriented so that, when the aiming device and the handle are coupled to one another, a bone fixation receiving hole in an intramedullary nail coupled to the handle is aligned with the guide opening, the aiming device further including a hollow elastic locking pin mounted therein, the aiming device including a pin opening extending thereinto along a pin opening axis transverse to the guide opening axis, a length of the pin opening is less than a thickness of the aiming device such that the pin opening defines a blind bore, the locking pin including a transverse portion extending away from the pin opening axis and into the guide opening to engage a protective sleeve received therein.

2. The system of claim 1, wherein the pin opening extends substantially perpendicular to the guide opening, the pin opening including a window formed in a side wall thereof, the window opening into the guide opening.

3. The system of claim 2, wherein the pin is press-fit into the pin opening.

4. The system of claim 1, wherein the pin is fixed to the aiming device via an adhesive.

5. The system of claim 1, wherein the pin is compressed when the sleeve is inserted through the guide opening.

6. The system of claim 1, wherein the aiming device is attached to the handle via a coupling element.

7. The system of claim 6, wherein the coupling element is a knob including a shaft received through both the handle and the aiming device.

8. The system of claim 1, wherein the aiming device and the handle are integrally formed.

9. An aiming device for guiding a bone fixation element, the aiming device extending from a proximal end to a distal end and comprising:
    a guide opening extending through the aiming device along a guide opening axis, the guide opening being sized and shaped to accommodate a protective sleeve therein, the guide opening located such that when the aiming device is coupled to a bone fixation device, the guide opening is aligned with a fixation element receiving hole of the bone fixation device;
    a pin opening extending through the aiming device along a pin opening axis, the pin opening axis extending transverse to the guide opening axis, a length of the pin opening is less than a thickness of the aiming device such that the pin opening defines a blind bore; and
    a hollow elastic locking pin mounted within the pin opening and including a transverse portion extending away from the pin opening axis into the guide opening to engage a protective sleeve inserted therein.

10. The aiming device of claim 9, wherein the a pin opening extends substantially perpendicular to the guide opening, the pin opening including a window formed in a side wall thereof, the window opening into the guide opening.

11. The aiming device of claim 10, wherein the pin is press-fit into the pin opening.

12. The aiming device of claim 9, wherein the pin is fixed to the aiming device via an adhesive.

13. The aiming device of claim 9, wherein the pin is compressed when the sleeve is inserted through the guide opening.

14. The aiming device of claim 9, wherein the bone fixation device is a bone plate.

15. The aiming device of claim 9, wherein the bone fixation device is an intramedullary nail.

* * * * *